(12) United States Patent
Jaeggi

(10) Patent No.: US 10,578,631 B2
(45) Date of Patent: Mar. 3, 2020

(54) SAMPLE CARRIER HANDLING DEVICE

(71) Applicant: Roche Diagnostics Operations, Inc., Indianapolis, IN (US)

(72) Inventor: Beat Jaeggi, Lucerne (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 425 days.

(21) Appl. No.: 15/440,120

(22) Filed: Feb. 23, 2017

(65) Prior Publication Data
US 2017/0254824 A1 Sep. 7, 2017

(30) Foreign Application Priority Data

Mar. 3, 2016 (EP) ..................................... 16158382

(51) Int. Cl.
*G01N 35/02* (2006.01)
*G01N 35/04* (2006.01)

(52) U.S. Cl.
CPC ........... *G01N 35/021* (2013.01); *G01N 35/04* (2013.01); *G01N 2035/047* (2013.01); *G01N 2035/0467* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,978,992 A | * | 9/1976 | Mulzet ...................... | B01L 9/00 198/801 |
| 5,013,529 A | * | 5/1991 | Itoh ..................... | G01N 35/1067 422/511 |
| 6,235,244 B1 | * | 5/2001 | Allen .................... | B01L 3/0275 422/525 |
| 6,837,359 B1 | | 1/2005 | Bessette | |
| 2012/0024661 A1 | | 2/2012 | Wilson et al. | |

FOREIGN PATENT DOCUMENTS

| | | |
|---|---|---|
| WO | 2013/072318 A1 | 5/2013 |
| WO | 2015/059620 A1 | 4/2015 |

OTHER PUBLICATIONS

Search Report dated Aug. 26, 2016, in Application No. EP 16158382.8, 9 pages.

* cited by examiner

*Primary Examiner* — Brian R Gordon
(74) *Attorney, Agent, or Firm* — Roche Diagnostics Operations, Inc.

(57) ABSTRACT

A sample carrier handling devices for manipulating a sample carrier is presented. The sample carrier carries a sample container containing a sample which is used in a diagnostics laboratory. The sample carrier handling device has a housing which is at least partially closed, defining a circumferential surface. A pull-push-element of the sample carrier handling device pulls, pushes, or pulls and pushes the sample carrier with an end-portion of the pull-push-element. The pull-push-element defines a central axis. The pull-push-element is arranged in the housing so that during a movement of the pull-push-element the central axis of the pull-push-element changes its direction while the end portion of the pull-push-element remains in an axis of motion.

14 Claims, 4 Drawing Sheets

SAMPLE CARRIER HANDLING DEVICE

CROSS-REFERENCE TO RELATED APPLICATIONS

This application claims priority to EP 16158382.8, filed Mar. 3, 2016, which is hereby incorporated by reference.

BACKGROUND

The present disclosure relates to a handling device to manipulate sample carriers on a transport system for a diagnostics laboratory.

The automation for handling samples of biological probes in a diagnostic laboratory is becoming more and more important.

Therefore, there is a need for to handle sample carriers that transport sample containers containing samples in an efficient and reliable way.

SUMMARY

According to the present disclosure, a sample carrier handling devices for manipulating a sample carrier is presented. The sample carrier is configured to carry a sample container containing a sample used in a diagnostics laboratory. The sample carrier handling device can comprise a housing at least partially closed and defining a circumferential surface and a pull-push-element configured to pull, push, or pull and push the sample carrier with an end-portion of the pull-push-element. The pull-push-element can define a central axis. The pull-push-element can be arranged in the housing so that during movement of the pull-push-element, the central axis of the pull-push-element can change its direction while the end portion of the pull-push-element can remain in an axis of motion.

Accordingly, it is a feature of the embodiments of the present disclosure to handle sample carriers that transport sample containers containing samples in an efficient and reliable way. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
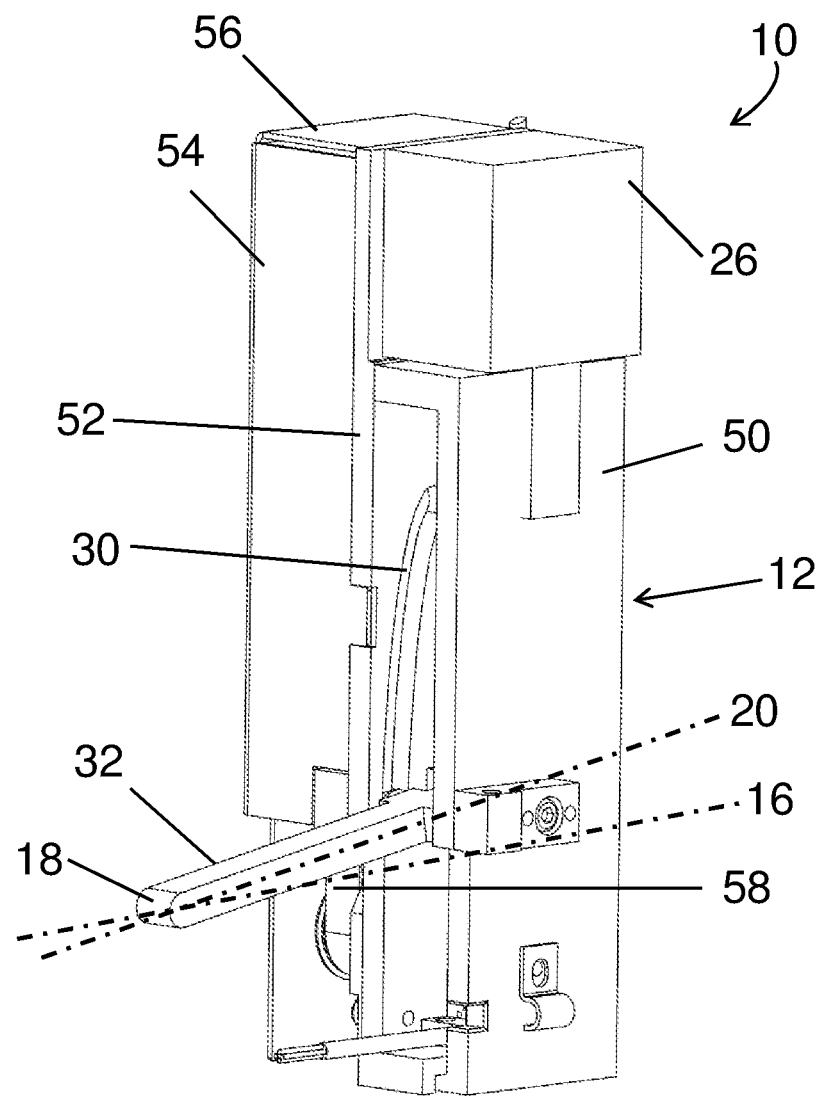
FIG. 1 illustrates a perspective view of a sample carrier handling device according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample carrier handling devices for manipulating a sample carrier which is configured to carry a sample container is presented. The sample container can contain a sample to be analyzed in a diagnostics laboratory. Also other samples, e.g. reactants or other materials used in the diagnostics laboratory, can be transported by the sample carrier. The sample carrier handling device can comprise a housing which can be at least partially closed. The housing can define a circumferential surface of the sample carrier handling device. The sample carrier handling device can further comprise a pull-push-element to pull, push, or pull and push the sample carrier at least with an end-portion of the pull-push-element. The pull-push-element can be arranged in the housing so that during movement of the pull-push-element, a central axis of the pull-push-element can change its direction while the end portion of the pull-push-element can remain in a level of motion. The central axis of the pull-push-element can, in one embodiment, be defined as the axis of longitudinal elongation of the pull-push-element. Therefore, the sample handling carrier device can be realized as a compact device with a reliable interaction with the sample carrier.

The end-portion of the pull-push-element can define during its movement an axis of motion in the level of movement and the end portion can be movable out of the circumferential surface along the axis of motion a maximum distance l between a first position and a second position of the pull-push-element.

In the first position, at least more than half of the pull-push-element can be placed inside the circumferential surface and, in the second position, at least more than half of the pull-push-element can protrude out of the housing, i.e. the circumferential surface. If the dimension of the circumferential surface along the axis of motion is m, the ratio of l over m can be, in one embodiment, in the range of about 1.1 to about 20 or, in another embodiment, in the range of about 1.2 to about 8 or, in yet another embodiment, in the range of about 1.4 to about 5.

In further embodiments, the ratio of l over m can be in the range of about 2 to about 10 or about 2 to about 5 or about 3 to about 5.

The end-portion configured to interact with the sample carrier, e.g. the end-portion, can comprise a detachable fixation element to interact with the sample carrier to pull, push, or pull and push the sample carrier. In one embodiment, the sample carrier can comprise a corresponding fixation device. The detachable fixation element can be a magnet, an electro-magnet, a movable hook, a suction-element, a snap, a gluing element, a hook-and-loop fastener element, and/or a contact surface configured to interact with the sample carrier.

The end-portion can comprise an abutting surface. The abutting surface can have a surface of a half-cylinder. The fixation element can be attached only to a partial surface of the abutting surface so that during the movement of the pull-push-element, the fixation element can come into contact with a sample carrier surface such as, for example, its corresponding fixation element at the first or second position and can detach from the sample carrier surface at the second or first position respectively, because the surface of the half-cylinder can roll off the surface of the sample carrier. For instance, the gluing element can be arranged on the abutting surface of the pull-push-element. This can allow the automatic fixation and detaching of the sample carrier to the pull-push-element to pull, push, or pull and push the sample carrier.

The handling device can comprise a link motion to guide the pull-push-element during its motion. In one embodiment, a guide bar of the motion link can either be realized by the push-pull-element itself or the guide bar of the motion link can be connected to the pull-push-element. A link motion as used here can be an element which can deflect the push-pull-element or can reel and unreel the pull-push-element.

The pull-push-element can be a flexible rod such as, for example, a chain or made out of flexible plastic such as, for example a gum. Flexible can mean that the rod can be deformed by the motion link but can remain rigid or can be supported when protruding out of the circumferential surface under usual environmental conditions appropriate to a diagnostics laboratory.

A driving unit can be connected to the pull-push-element. The driving unit can be connected with a wheel arranged to contact the flexible rod in order to move the flexible rod in a guide bar of the link motion. For instance, the wheel can be a gear that can mesh with pull-push-element as a chain or the wheel can have a profile wherein a ratio of a circumferential surface of the flexible rod can be in contact with.

The pull-push-element can be a rigid rod. Rigid can mean that the rod may not change its shape under gravitational forces in usual environmental conditions. In one embodiment, the rigid rod can be connected at its other end portion with a vertical movable carriage and the motion link can be connected to the rigid rod with a link block at a point of deviation of the rigid rod. Vertical can mean substantially perpendicular with respect to the axis of motion. "Substantially perpendicular" can mean for the following and the scope of this disclosure within a range of about 80 to about 100 degrees. In one embodiment, it can mean about 85 to about 95 degrees.

A diagnostics laboratory sample carrier transport system is presented. The diagnostics laboratory sample carrier transport system can comprise a transport device, a sample carrier and a sample carrier handling device as described above.

The transport device can comprise a transport belt to carry the sample carrier. The sample carrier handling device can be connected to the transport belt so that the sample carrier can move substantially perpendicular with respect to a direction of motion of the transport belt. This can allow reliably loading and unloading of the sample carrier to and from the transport belt in a compact arrangement.

The diagnostics laboratory sample carrier transport system can comprise a further transport belt arranged substantially parallel or substantially perpendicular to the transport belt. The carrier handling device can be connected to the transport belt so that the sample carrier can move from the transport belt to the further transport belt and/or from the further transport belt to the transport belt.

The inventive diagnostics laboratory sample carrier transport system can comprise a transport surface supporting the transport carriers. The sample carrier handling device can be connected to the transport surface to push, pull, or push and pull the sample carrier onto or from the transport surface. This can allow easy and reliable loading sample carriers with or without samples in the sample carriers onto and/or from the transport surface in a compact arrangement.

A diagnostics laboratory system is presented. The diagnostics laboratory system can comprise a pre-analytic system, a post-analytic system and a analyzer system and a diagnostic laboratory sample carrier transport system as described above.

At least one sample carrier handling device can be connected to the diagnostics laboratory sample carrier transport system so that the sample carrier handling device can be configured to transfer sample carrier between at least two out of the list of: a pre-analytic system, a post-analytic system, an analyzer system, a diagnostic laboratory sample carrier transport system, and a further diagnostic laboratory sample carrier transport system. This can allow easy, reliable transfer of sample carriers with or without samples from one device to another device of the diagnostic laboratory system. Usually, the different devices can use their proper transport system, so that the sample carrier can be transferred between different transport systems of the diagnostics laboratory system and the proper transport systems by the sample carrier handling device. However, other embodiments can be feasible.

Figure 2:
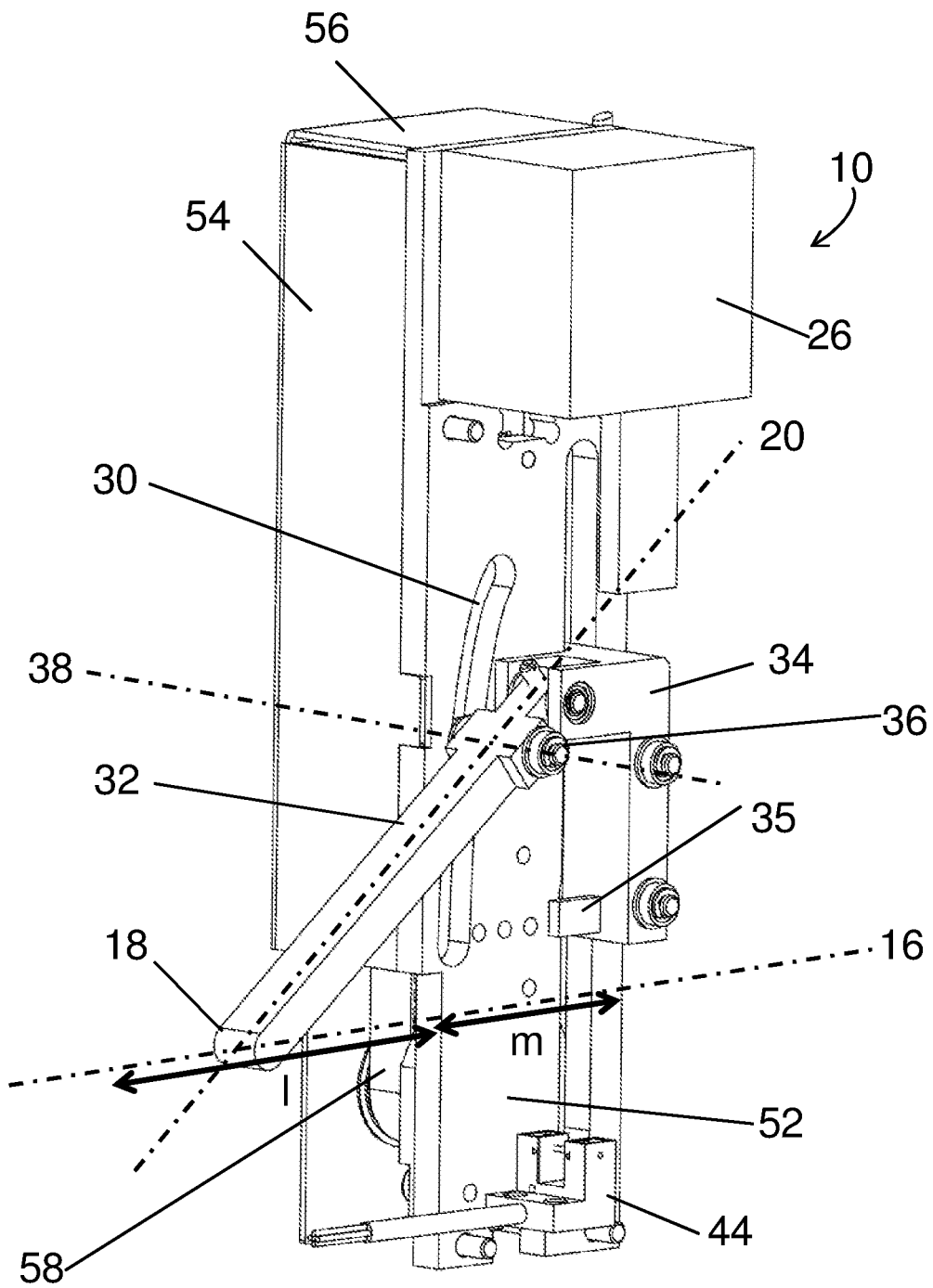
FIG. 2 illustrates a perspective view of the embodiment shown in FIG. 1 wherein one side wall is omitted according to an embodiment of the present disclosure.

FIGS. 1 and 2 show a perspective view of one embodiment of a sample carrier handling device 10. The sample carrier handling device 10 can comprise a housing 12. The housing 12 can be assembled out of several parts. Some of these parts are shown in the Figures. These parts can be connected together by conventional connecting technologies such as screws, gluing, soldering, welding and/or other known technologies. The housing 12 can have some open surface areas, i.e. the surface of the housing 12 may not be totally closed. The outer surfaces of the parts of the housing 12 can span a circumferential surface of the housing 12 which can have approximately a shape of a cuboid.

Some parts of the housing 12 shown in FIG. 1 are a first side wall 50, a middle wall 52, a front wall 54 and a second side wall 56. A portion of the second side wall 56 can be bent to form a portion of a top surface. The edge of this bent portion can abut an end portion of the middle wall 52. A front wall 54 can be arranged between the second side wall 56 and the middle wall 52. The second side wall, the front wall 54 and the middle wall can span a belt drive part of the housing 12 in which a belt drive 58 can be arranged.

The first side wall 50 can be u-shaped facing with the edges of the arms of the u to the middle wall 52 so that a portion of the middle wall 52 and the first side wall 50 can build up a frame. This frame can define a link-motion part of the housing.

In this frame, the pull-push-element can be movably fixed. In this embodiment, the pull-push-element can be a rigid rod 32. An end portion 18 of the rigid rod 32 can protrude from the circumferential surface. The other end portion of the rod 32 opposite to the end portion 18 can be fixed to a carriage 34.

The first side wall 50 can be shorter than the middle wall 52 so that a rectangular recess can be created. In this recess, a driving unit 26 can be arranged. A surface of the driving unit 26 can fit at least partially into the cuboid-shaped circumferential surface of the housing 12. The driving unit 26 can be connected to the belt drive 58 to move the belt drive 58 in both possible directions.

The carriage 34 can be arranged in a slit 53 of the middle wall so that it can extend in spatial length in the link-motion part and the belt-drive part of the housing 12. In the belt drive part of the housing 12, the carriage 34 can be fixed to the belt drive 58 so that the belt drive can move the carriage 34 in the slit 53 of the middle wall. The slit 53 can define the direction of motion of the carriage 34. In the link motion part, the carriage can accept the other end portion of the rod 32 so that the end portion can remain rotatable around a carriage axis. This carriage axis can be arranged substantially perpendicular to the elongation of the slit 53 in the middle wall.

The carriage 34 can comprise a distant portion 35 which can engages with a sensor element 44 to detect an end-point of the movement of the carriage 34. This sensor element 44 can be, in one embodiment, a light barrier which can be interrupted by the distant portion.

Adjacent to the other end portion of the rod 32, the rod 32 can comprise two link blocks 36. The link blocks can define an axis of deviation which can be substantially parallel to the carriage axis. The two link blocks can engage into opposite guide bars 30 of the middle wall 52 and the side wall 50. The guide bars 30 and the link blocks 36 can define a link motion. The guide bars can be designed as grooves in the wall or as slits.

The carriage 34 can move the rod 32 in the link motion so that the end portion 18 of the rod 32 can move along an axis of motion 16 which can be, in one embodiment, straight and substantially perpendicular to the slit 53 in the middle wall. In one embodiment, straight can mean that the end portion 18 may not change its distance during its motion to a level of motion substantially perpendicular to the slit 53 within a range of about 0 cm to about 2 cm, in another embodiment, within a range of about 0 to about 1.5 cm, and in yet another embodiment, in a range of about 0 to about 1.0 cm or about 0 to about 0.5 cm.

Due to the link motion arrangement within the housing 12, the end portion 18 can move a distance along the axis of motion 16 which can be greater than the width of the housing 12 along the axis of motion.

For the embodiment shown in FIGS. 1 and 2, the guide bar 30 can be curved so that the link motion can provide that during movement of the carriage 34, the end portion 18 of the rigid rod 32 can follow the axis of motion 16 within the accuracy of manufacturing. At a first position of the rigid rod 32 within the housing, the carriage 34 can be moved to an upper position and the rigid rod can mainly be placed inside the circumferential surface. At a second position, the carriage 34 can be moved to a lower position. At this position, the distant portion of the carriage can engage with the sensor element 44, i.e., can interrupt the light barrier. This can generate a signal to indicate that the carriage is at its lower position. The rigid rod 32 can at this second position be protruding a maximum length l out of the circumferential surface. The dimension of the circumferential surface in the direction of the axis of motion 16 can be m. The ratio of l over m can for this embodiment be in the range of about 1.2 to about 3.

The end portion 18 can have a shape of half of a cylinder surface which its axis of rotation substantially perpendicular to the central axis 20 of the rod 32. In other embodiments, this cylindrical surface can comprise a further element, or elements, configured to interact with the surface of a sample carrier contacting the end portion 18. For instance a magnet, an electro-magnet, a movable hook, a suction-element, a gluing element, a hook-and-loop fastener element, and/or a contact surface can be arranged at the end portion 18 configured to interact with a correspondent element at the sample carrier surface.

Figure 4:
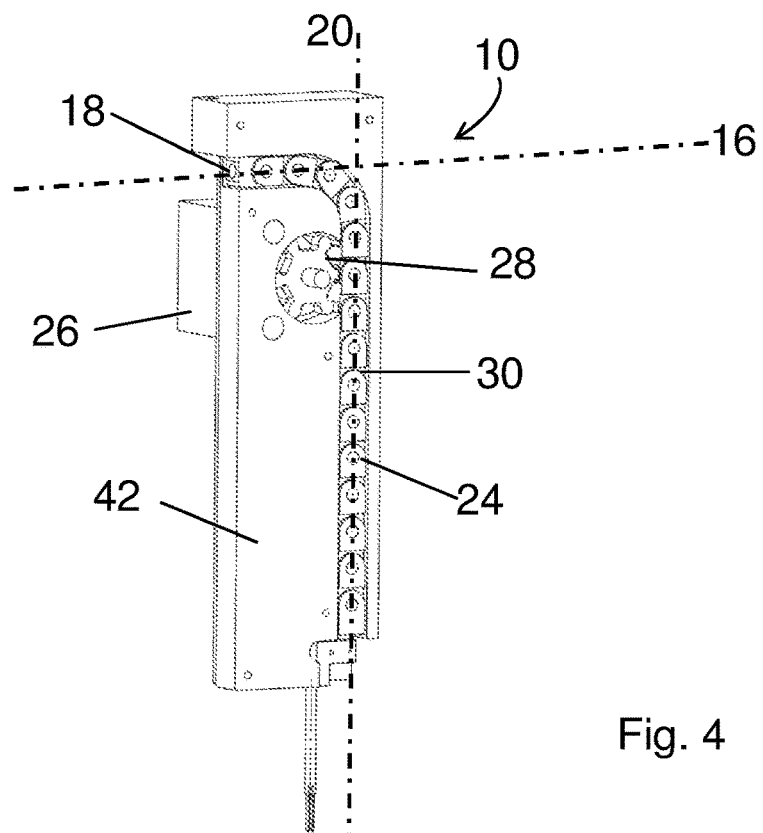
FIG. 4 illustrates a perspective view of the embodiment shown in FIG. 3 wherein one side wall is omitted according to an embodiment of the present disclosure.
Figure 3:
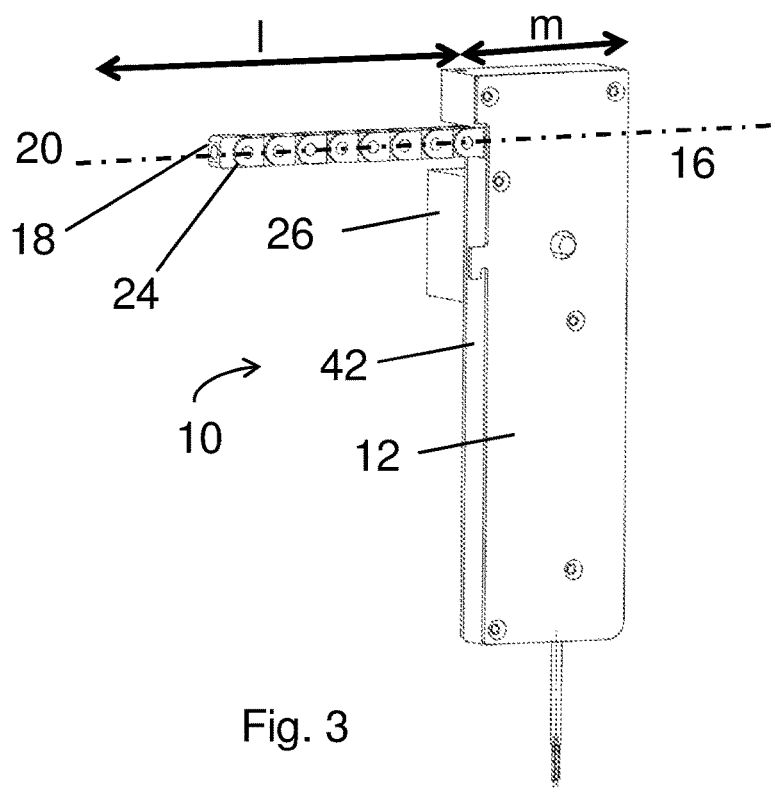
FIG. 3 illustrates a perspective view of a sample carrier handling device according to another embodiment of the present disclosure.

FIGS. 3 and 4 present a second embodiment of the sample carrier handling device 10. In this embodiment, the pull-push-element can be realized as a chain. The central axis 20 of the chain 24 can be defined as the axis on which most of the elements of the chain 24 can be aligned.

The chain 24 can be guided in a guide bar 30 of a body 42 of the sample carrier handling device 10. The body 42 can also define a housing 12 which can also realize a circumferential surface. The body 42 can comprise further a gear-wheel 28 arranged to mesh with the chain 24. A driving unit 26 can be fixed to the body 42 and interact with the gear wheel 28 to rotate the gear wheel 28. The guide bar can deviate the chain 24 within the body 42 to perform a 90 degree change of movement. Therefore the central axis of the chain 24, as defined above, can change its direction, during movement of the chain 24.

An end portion of the chain 24 can protrude out of the body 42 to pull, push, or push and pull the sample carrier along the axis of motion. Due to the deviation of the chain in the body 42, the maximum distance of motion of the end portion of the chain 24 can be greater the dimension of the body 42 along the axis of motion 16.

The sample handling carrier device 10 shown in this embodiment can be arranged so that the chain elements block each other when they protrude out of the body 42. So the chain cannot be deviated by gravity in an unfortunate way. In another option, the chain 24 can slip on a surface provided by the sample carrier transport system. The surface can supports the chain element to avoid deviation.

In FIG. 3, the chain can protrude from the body 42 at a maximum length l. Here the central axis 16 of the chain and the axis of motion 20 can coincide. The body 42, i.e. the circumferential surface, can have a length m along the axis of motion 16. The ratio of l over m can be for this embodiment as high as about 20 for a reasonable height of the body 42, which can be the dimension substantially perpendicular to the axis of motion 16.

In FIG. 4, the chain can completely be within the body 42 and the central axis 20 of the chain 24 can be substantially perpendicular to the axis of motion 16 along which the end portion 18 of the chain 24 can move.

In further embodiments, the end portion of the chain can comprise a further element, or elements, configured to interact with the surface of a sample carrier contacting the end portion. For instance a magnet, an electro-magnet, a movable hook, a suction-element, a gluing element, a hook-and-loop fastener element, and/or a contact surface can be arranged at the end portion configured to interact with a correspondent element at the sample carrier surface.

Figure 5:
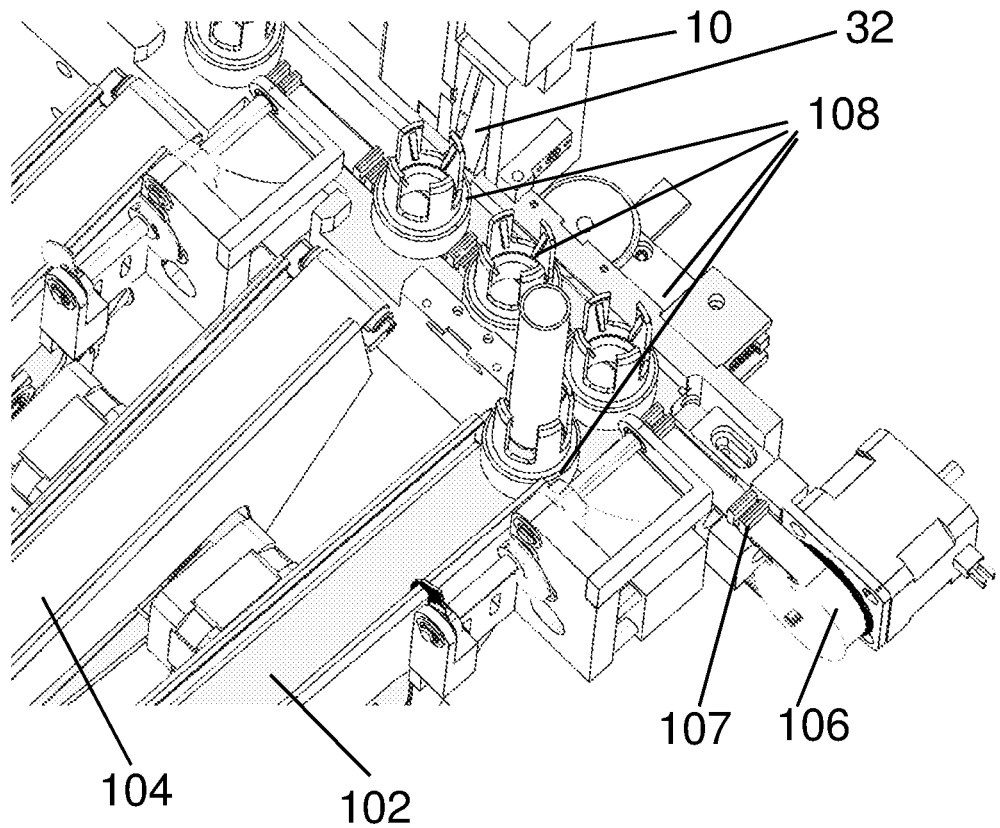
FIG. 5 illustrates a perspective view of a detail of an embodiment of a diagnostic laboratory sample carrier transport system according to an embodiment of the present disclosure.

FIG. 5 shows a detail of a view on a diagnostics laboratory sample carrier transport system. An incoming belt 102 can transport sample carriers 108 with or without a sample containers 110 to an interconnecting belt 106. The incoming belt 102 can push the sample carrier 108 onto the interconnecting belt 106. To push the sample carriers 108 from the interconnecting belt to an outgoing belt 104, a sample carrier handling device 10 can be arranged in front of the outgoing belt 104. This can realize a very compact reliable way to handle the sample carriers for connecting the incoming belt 102 and the outgoing belt 104.

The interconnecting belt 106 can be divided by protruding portions 107 into support sections adapted to receive one sample carrier 108. The protruding portions 107 can be formed as a double ripple within the interconnecting belt 106.

The sample carrier 108 can comprise a cylindrical shaped base and elongated finger-elements. The end portion of the pull-push-element can strike against this surface of the cylindrical shaped base to move the sample carrier 108 from the interconnecting belt 106 to the outgoing belt 104. The elongated finger elements can comprise flexible elements to support sample containers 110, which can then be transported within the sample carriers 108 on the transport system.

Figure 6:
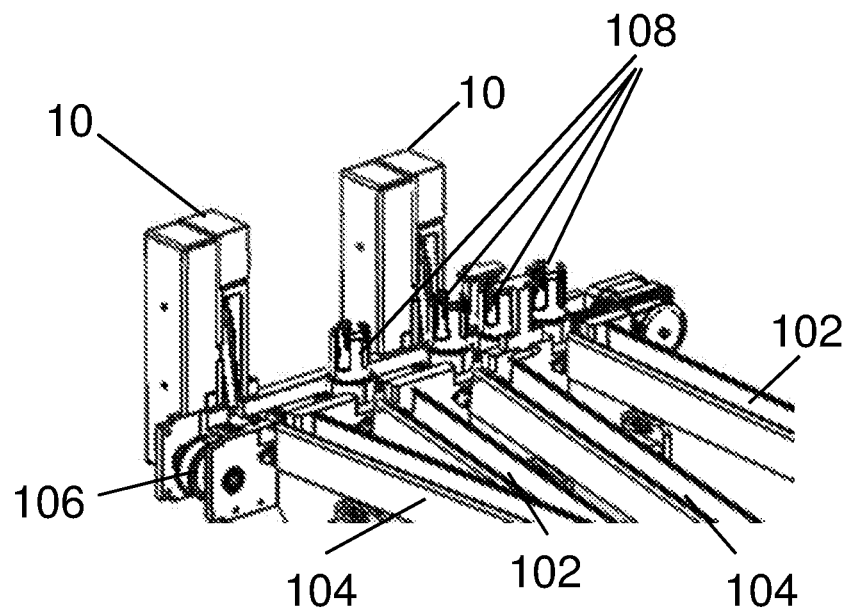
FIG. 6 illustrates a further perspective view of the embodiment shown in FIG. 5 according to an embodiment of the present disclosure.

FIG. 6 shows another view on a bigger detail of the diagnostics laboratory sample carrier transport system shown in FIG. 5. A further incoming belt 102 and outgoing belt 104 are shown. Also in front of the further outgoing belt, a further sample carrier handling device 10 can be placed. On the interconnecting belt 106, four sample carriers 108 are shown.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A sample carrier handling devices for manipulating a sample carrier, wherein the sample carrier is configured to carry a sample container containing a sample used in a diagnostics laboratory, the sample carrier handling device comprising:
    a housing, which is at least partially closed, defining a circumferential surface;
    a pull-push-element arranged in the housing to perform a movement and configured to pull, push, or pull and push the sample carrier with an end-portion of the pull-push-element during the movement, wherein the pull-push-element defines a central axis as its axis of longitudinal elongation, wherein during the movement of the pull-push-element, the central axis of the pull-push-element changes direction while the end portion of the pull-push-element remains in an axis of motion defined by a movement of the end portion, and wherein the pull-push element is a chain.

2. The sample carrier handling device according to claim 1, wherein the pull-push-element is arranged in the housing so that the end portion is movable out of a circumferential surface of the housing along the axis of motion a maximum distance l between a first position and a second position of the pull-push-element and wherein a measure in one direction of the circumferential surface along the axis of motion is m.

3. The sample carrier handling device according to claim 2, wherein the ratio of l over m is in the range of 1.1 to 20.

4. The sample carrier handling device according to claim 2, wherein the ratio of l over m is in the range of 1.2 to 8.

5. The sample carrier handling device according to claim 2, wherein the ratio of l over m is in the range of 1.4 to 5.

6. The sample carrier handling device according to claim 1, wherein the end-portion comprises one of the list of: a magnet, an electro-magnet, a movable hook, a suction-element, a gluing element, a hook-and-loop fastener element, and a contact surface configured to interact with the sample carrier.

7. The sample carrier handling device according to claim 1, further comprising,
    a link motion comprising at least one guide bar and at least two link blocks to guide the end-portion of the pull-push-element along the axis of motion.

8. The sample carrier handling device according to claim 7, further comprising,
    a wheel in the housing; and
    a driving unit, wherein the driving unit is connected to the wheel which is arranged to contact with the chain to move the chain in the at least one guide bar of the link motion.

9. A diagnostics laboratory sample carrier transport system, the diagnostics laboratory sample carrier transport system comprising:
    a transport device;
    a sample carrier; and
    a sample carrier handling device according to claim 1, wherein the sample carrier handling device is connected to the transport device and is configured to pull, push, or push and pull the sample carrier.

10. The diagnostics laboratory sample carrier transport system according to claim 5, wherein the transport device comprises a first transport belt to carry the sample carrier, wherein the sample carrier handling device is connected to the first transport belt so that the sample carrier moves perpendicular with respect to a direction of motion of the first transport belt.

11. The diagnostics laboratory sample carrier transport system according to claim 10 further comprising,
    a second transport belt arranged in parallel, or perpendicular, to the first transport belt, wherein the sample carrier handling device is connected to the first transport belt so that the sample carrier moves from the first transport belt to the second transport belt and/or from the second transport belt to the first transport belt.

12. The diagnostics laboratory sample carrier transport system according to claim 9, further comprising,
    a transport surface supporting the sample carriers, wherein the sample carrier handling device is connected to the transport surface to push, pull, or push and pull the sample carrier on or from the transport surface.

13. A sample carrier handling devices for manipulating a sample carrier, wherein the sample carrier is configured to carry a sample container containing a sample used in a diagnostics laboratory, the sample carrier handling device comprising:
    a housing, which is at least partially closed, defining a circumferential surface;

a pull-push-element arranged in the housing to perform a movement and configured to pull, push, or pull and push the sample carrier with an end-portion of the pull-push-element during its movement, wherein the pull-push-element defines a central axis as its axis of longitudinal elongation, wherein the pull-push-element is arranged in the housing so that during movement of the pull-push-element, the central axis of the pull-push-element changes direction while the end portion of the pull-push-element remains in an axis of motion defined by a movement of the end portion; and a link motion to guide the pull-push-element, the link motion comprises opposite guide bars and two link blocks, wherein the pull-push-element is a rod comprising the two link blocks which engage into the opposite guide bars.

14. The sample carrier handling device according to claim 13, wherein the rod is rigid.

* * * * *